United States Patent [19]

Brooks

[11] Patent Number: 5,116,388
[45] Date of Patent: May 26, 1992

[54] METHOD OF BLEACHING AND CONDITIONING HAIR, BLEACH PACKET AND BLEACHING SOLUTIONS

[75] Inventor: Geoffrey J. Brooks, Livingston, N.J.

[73] Assignee: Gijj, Inc., S. River, N.J.

[21] Appl. No.: 606,435

[22] Filed: Oct. 29, 1990

Related U.S. Application Data

[62] Division of Ser. No. 383,857, Jul. 21, 1989.

[51] Int. Cl.$^5$ .............. A61K 7/13; A61K 7/06; D06L 3/02
[52] U.S. Cl. .................................. 8/405; 8/111; 8/127.51; 8/406; 252/186.25; 424/67
[58] Field of Search ............... 8/111, 127.51, 405, 8/406; 424/67; 252/186.25

[56] References Cited

U.S. PATENT DOCUMENTS

| | | | |
|---|---|---|---|
| 3,413,229 | 11/1968 | Bianco et al. | 252/90 |
| 3,892,905 | 7/1975 | Albert | 252/90 |
| 3,931,912 | 1/1976 | Hsiung | 222/94 |
| 4,247,537 | 1/1981 | Lunn et al. | 8/111 |
| 4,283,384 | 8/1981 | Jacquet et al. | 424/47 |
| 4,506,783 | 5/1985 | Morganroth | 206/581 |
| 4,661,299 | 7/1986 | Wolfram | 132/7 |
| 4,689,217 | 8/1987 | Restaino et al. | 424/70 |
| 4,690,817 | 9/1987 | Davis et al. | 424/70 |
| 4,764,363 | 8/1988 | Bolich, Jr. | 424/47 |
| 4,835,314 | 5/1989 | Konrad et al. | 564/441 |
| 4,933,177 | 6/1990 | Grollier et al. | 424/74 |
| 4,950,302 | 8/1990 | Clausen et al. | 8/409 |
| 4,975,093 | 12/1990 | Clausen et al. | 8/428 |

Primary Examiner—A. Lionel Clingman
Assistant Examiner—William S. Parks
Attorney, Agent, or Firm—Weingram & Zall

[57] ABSTRACT

A method of bleaching hair comprising:

(a) providing a bleach packet comprising a predetermined effective amount of bleach composition to bleach a person's hair, enclosed in a water soluble enclosure;
(b) providing an activator solution comprising water and an effective amount of activator to activate the bleach;
(c) contacting the bleach packet with the activator solution, to thereby dissolve the water soluble enclosure and activate the bleach to form a bleach solution;
(d) applying the bleach solution to the hair to thereby bleach the hair.

The preferred water soluble enclosure is a water soluble polymeric material comprising polyvinyl alcohol and compositions similar thereto.

It has also been found that damage to hair attending the coloring or bleaching process may be prevented or retarded by treating said hair with a solution of the water soluble polymer.

This invention is further directed to a bleach packet comprised of a predetermined effective amount of bleach to bleach a person's hair enclosed in a water soluble enclosure.

In another aspect of this invention a novel hair bleaching solution is provided comprising a water solution of an activated bleach in combination with a conditioning amount of a water soluble polymer which simultaneously conditions and bleaches the hair.

5 Claims, No Drawings

METHOD OF BLEACHING AND CONDITIONING HAIR, BLEACH PACKET AND BLEACHING SOLUTIONS

This is a divisional of copending application Ser. No. 383,857, filed on Jul. 21, 1989.

BACKGROUND OF THE INVENTION

Field of the Invention

This invention relates to a method of bleaching hair comprising the use of a novel bleach packet, in particular, a bleach packet comprising an effective amount of hair bleach enclosed by a water soluble enclosure, e.g. polyvinyl alcohol. This invention further relates to a method of conditioning and minimizing damage to hair during the bleaching or coloring of hair.

Prior Art

It is well known to bleach hair and reviews of the techniques and bleaching systems used to achieve these effects are readily available. Thus, for example, the subject is discussed in the publication, Perfumes, Cosmetics and Soaps, (Vol. III, Modern Cosmetics, Chapter 7, by W. A. Poucher, revised by George M. Howard, 8th Ed., (1976) (J. Wiley & Sons, New York); and the publication Harry's Cosmeticology, Vol. I, by R. G. Harry, 6th Ed., (1973), (Leonard Hill Books, London).

Powdered hair bleach compositions are known in the hair coloring art which, when mixed with a developer or activator, such as hydrogen peroxide of various strengths or volumes, can be applied to the hair to lighten its color.

Beauty Salons, including barber shops and hairstyling establishments, have traditionally used powdered bleach compositions for lightening and streaking the hair to create a fashionable appearance. Typically, these bleach products are sold in large containers and comprise an alkaline bleaching powder which is scooped out using a plastic scoop or measuring device and stirred into a water solution of the activator, e.g. Hydrogen peroxide. A reaction occurs between the powdered bleach, which comprises a powerful oxidizing agent, and the activator to liberate free oxygen which acts to bleach the hair. The bleaching solutions are then immediately used to bleach the hair.

Because of the instability of aqueous alkaline peroxide solutions, as well as because of the interaction of hydrogen peroxide with other ingredients in most of these bleaching compositions, it has been essential to package such compositions so that the ingredients are contained in two separate containers, in effect, separating the aqueous acidic hydrogen peroxide from, the powdered bleaching composition comprising, for example, the bleaching or oxidizing agent. Typical of such compositions are hair dyes, bleaches, hair lightening agents, hair lightening shampoos, or setting compositions and the like.

The powdered bleaches contain high levels of highly reactive materials which function as oxidizers. These compositions must thus be packaged in rigid airtight and watertight packages, such as glass, plastic coated metal or a rigid high density plastic (such as polyethylene, polypropylene, polyvinyl chloride, etc.) with extra thick walls. The contents thereof are scooped out using a disposable plastic measuring cup. An alternative approach has been to use a laminated pouch package, consisting of sandwiches of various plastics around aluminum and paper films to provide proper barrier function. These packages are cut open and mixed with the activator solution.

There are several problems associated with the use of such powdered bleaches and the procedures used for bleaching hair. A primary problem is exposure of the user and his surroundings to the chemical dust and fumes therefrom. Opening a container of finely ground bleach material, measuring an amount of the bleach material and transferring the measured amount from the container to the equipment where the bleach material is contacted and mixed with water and an activator can generate air born dust which contacts the user and contaminates the area. The bleach dust may be irritating to the eyes and mucous membranes of the nose and throat of the user.

Another problem in using this type of hair bleach is the accuracy of measurement, Clearly, overuse of bleach is costly. Use of a too weak or too strong a bleaching solution will not produce the results desired by the hair dresser. It may be extremely difficult to accurately measure and transfer the powdered bleach material which may have become compacted and lumpy in the container due to the high affinity of the bleach for moisture. Additionally, when the bleach absorbs moisture it will react therewith, reducing the free oxygen, making the product less efficacious.

Further, after the chemical has been used, the user is faced with the problem of disposing of the container in which the chemical bleach was delivered. Residual amounts of the material may be retained in the container creating a pollution problem which is potentially hazardous to humans, animals, or merely unpleasant and unsightly.

Additionally, when the reaction of the bleach with the activator solution occurs, particularly at the surface of the solution, a substantial amount of fumes are generated which are offensive to the salon operator and customers, possibly hazardous to a person's health and, at the very least make it undesirable to use these products as often as they could or should be used.

Further, bleaching solutions prepared for use cannot be bottled and stored prior to use due to the fact that the shelf life of the activated bleach is fairly limited.

Still further, many of the hair coloring procedures, e.g. bleaching, require the use of an oxidizing agent which tends to damage hair and make it more "porous". In some instances the hair is subjected to multiple treatments with compositions containing oxidizing agents and the damage may be compounded.

A variety of adverse effects on the structure of the hair occur during such treatment. Hair coloring treatments, e.g. bleaching may seriously weaken or embrittle the hair so that it will break off in wet or dry conditions; cause hair to lose its normal resilience when highly bleached, so that it feels like sponge or rubber, stretches like a thin rubber filament if pulled, breaks if stretched beyond the elastic limit, and in dry condition, is brittle and snaps off if bent; and reduces the ability of the hair to take up color in the normal manner. In many cases the scalp may also be deleteriously effected by contact for too long a period of time with the bleachants used on the hair.

In effect, any product that changes the structure or the color of the hair does so by a chemical reaction which changes the chemical nature of the hair. Hair at its best, when it is undamaged is flexible, and has an excellent feel and shine. All chemical processes performed on the hair, e.g., bleaching, waving and dyeing, adversely affect the structure, the integrity and the general well being of the hair. There has been substantial development on the addition of conditioners to dyes and waving products to improve the after feel of the hair. In contrast there have been very few developments on using conditioners in powdered bleaches to prevent damage to hair.

The following ar the relevant references uncovered relating to this invention:

U.S. Pat. No. 4,522,738 to Magid et al (1985), describes a toilet bowl cleaner having inner and outer water soluble envelopes. The inner envelope contains a basic material. The outer envelope contains the inner envelope and an acidic material. In use, the outer envelope dissolves releasing the acidic material to clean the toilet bowl. The inner envelope then dissolves, releasing the basic material contained therein, to neutralize the toilet bowl water. The preferred polymeric film bag is a polyvinyl alcohol. Other bags may be utilized, for example, methyl cellulose, carboxymethylcellulose.

U.S. Pat. No. 3,472,604 to Dasher et al (1989) describes a process for preventing or retarding damage to hair during coloring operations, e.g., bleaching or dyeing with oxidation dyes, by simultaneously polymerizing a vinylic monomer on the hair. The polymerization is brought about by the oxidizing agent used in the bleaching or dyeing operation.

U.S. Pat. Nos. 3,784,005 and 3,902,596 to McVav, (1975) describes a package which contains materials to be added to a resin formulation, the package containing a vinylic monomer. A thin walled plastic envelope which is soluble in the resin formulation is used. Preferably the envelope is made of polystyrene film. The primary use for this packaging is for compounding polyester resins.

U.S. Pat. Nos. 3,931,912 (1976) and 3,651,931 (1972), to Hsiung, describes a pressure packaged liquid composition which contains two compositions, one of which includes hydrogen peroxide. The compositions are adapted to be mixed while being discharged.

U.S. Pat. No. 4,010,872 to Lozano et al, (1977), describes a package wherein two compositions are maintained isolated from each other within a container. One composition comprises an oxidation hair dye and the other is hydrogen peroxide. A means is provided to release each to dispense a mixture as a hair dye.

U.S. Pat. No. 4,506,783 and 4,114,632 to Morganroth, (1985) describe various packaging for bleaching compounds.

U.S. Pat. No. 4,327,751 to Evans, (1982) describes a composition for lightening hair which comprises an alkaline bleaching system in an amount of finely divided solid polyolefin polymer. The polymeric material acts as a lightening decelerator.

U.S. Pat. Nos. 3,912,808, 3,986,825 and 4,027,008 to Sokol, are of general interest in that they disclose hair bleaching compositions which comprise polymers to improve the surface characteristics of hair.

U.S. Pat. No. 3,300,546 to Baechtold, describes water soluble, water and heat sealable film materials suitable for use as a water soluble wrap or for fabrication into water soluble envelopes. This reference teaches the packaging of household materials such as dry bleach, water softening powders, etc. for use in dishwashers or laundry machines.

U.S. Pat. Nos. 3,374,195 and 3,413,229, to Bianco et al, describe polyvinyl alcohol compositions containing a plasticizer useful for packaging, in particular packets for use with laundry compositions.

U.S. Pat. No. 3,892,905 to Albert describes films which are readily soluble in cold water made from a mixture of polyvinyl alcohol or polyvinyl pyrrolidone and their use for packaging cleaning products, such as bleaches.

None of the foregoing references disclose a packet comprising a hair bleach composition in a water soluble enclosure, the use of such package to prepare a novel aqueous bleaching solution, and the use of said solution to bleach hair and produce an unexpected conditioning of said hair.

OBJECTS AND SUMMARY OF THE INVENTION

It is an object of this invention to provide a method of bleaching hair which eliminates irritating dust fumes generated when producing a bleaching solution used therefor.

It is another object of this invention to provide a bleach packet which can be used to conveniently and safely produce a bleaching solution and eliminate the problems associated with prior art methods.

It is still another object of the present invention to provide a process for conditioning the hair during the bleaching or coloring of the hair and improving the luster of the hair.

It is a further object of this invention to provide a novel bleaching solution which not only bleaches the hair but additionally conditions the hair, i.e., prevents frizziness associated with the use of bleaching solutions.

It is yet a further object of this invention to provide a convenient to use bleach packet which, when added to an activator solution for the bleach, produces a bleaching solution which not only bleaches hair but prevents frizzing.

A still further object of this invention is to provide an additive package comprising a soluble envelope formed of a thin sheet of synthetic organic polymeric material for use in preparing aqueous compositions for bleaching.

A still further object of this invention is to provide an additive package which may be used to incorporate bleach and other additives in an aqueous composition for bleaching.

Still another object of this invention is to provide an additive package containing one or more additives which coact synergistically with the material from which the package is made during use to provide for the treatment and protection/conditioning of the hair.

Yet another object is to provide the user of hair bleach, e.g. a hairdresser, an accurate predetermined effective amount of bleach for use, thus providing greater control of either the bleaching, streaking, or highlighting process to enable the user to determine the type of results they wish to achieve on their clients' hair.

It is another object of the present invention to provide an additive package for use in bleaching which overcomes the foregoing problems and provides an air-tight water soluble package of essentially unlimited shelf life, which is simple and easy to manufacture and which will completely dissolve in a short time in an aqueous solution.

The method of this invention is directed to bleaching hair comprising:

(a) providing a bleach packet comprising a predetermined effective amount of bleach composition to bleach a person's hair, enclosed in a water soluble enclosure;

(b) providing an activator solution comprising water and an effective amount of activator to activate the bleach;

(c) contacting the bleach packet with the activator solution, to thereby dissolve the water soluble enclosure and activate the bleach to form a bleach solution;

(d) applying the bleach solution to the hair to thereby bleach the hair.

The preferred water soluble enclosure is a water soluble polymeric material comprising polyvinyl alcohol and compositions similar thereto.

It has also been found that damage to hair attending the coloring or bleaching process may be prevented or retarded by treating said hair with a solution of the water soluble polymer.

This invention is further directed to a bleach packet comprised of a predetermined effective amount of bleach to bleach a person's hair enclosed in a water soluble enclosure.

In another aspect of this invention a novel hair bleaching solution is provided comprising a water solution of an activated bleach in combination with a conditioning amount of a water soluble polymer which simultaneously conditions and bleaches the hair.

DETAILED DESCRIPTION OF THE INVENTION

In the preferred embodiment of this invention, a bleach packet is provided comprising a predetermined effective amount of a bleach composition to bleach a person's hair, enclosed in a water-soluble enclosure. This bleach packet is then immersed below the surface and dissolved in a solution of activator, e.g. hydrogen peroxide, to form a bleaching solution. The bleaching solution is then applied to the hair to bleach the hair. Preferably the water-soluble enclosure is a water-soluble polymer comprising polyvinyl alcohol which dissolves in the bleaching solution and when applied to the hair conditions the hair while being bleached.

As used herein, the term "bleaching composition" is used in its broad sense and is intended to encompass a single oxidizing or bleaching agent, as well as a combination of oxidizing or bleaching agents, as well as other ingredients. Moreover, it is also intended to cover complex compositions which include other components which may or may not be active ingredients. Thus, the term "bleaching composition" is intended to apply to compositions which contain, in addition to an active oxidizing or bleaching agent, such things as, by way of example, thickeners, carriers, surface active agents, basic materials, buffers, organic solvents, alkalizing agents, antioxidants, sequestering agents, perfumes, dyes, surfactants and conditioners.

Included within this invention are the use of other compounds which are capable of being oxidized to yield colored oxidation products. Such compounds have been widely used by cosmetic chemists in developing hair dyeing products and are generally referred to as oxidation hair dyes. The most common of such products are based upon aromatic compounds which are capable in an alkaline medium of rapid oxidation by an oxidizing agent, (activator) such as hydrogen peroxide, to yield colored byproducts having color shades which have a high degree of consumer appeal on application to human hair. Products based upon this concept are also customarily packaged with an alkaline system containing a dye chemical and hydrogen peroxide in separate packages which are then mixed prior to use.

Thus, more specifically, the term "bleaching composition" may include the intermediate for an oxidation hair dye. This intermediate is capable of reacting, i.e., polymerizing, in an alkaline medium with hydrogen peroxide to yield a colored material which is adapted to safe application to human hair to change its color. Typical chemicals include aromatic nitro and/or amino compounds such as o- and p-phenylenediamine, 2,4-diamino anisol, p- and m-toluylene diamine, nitro substituted, o-, m- and p-phenylenediamine, o- and p-aminophenol and nitro-substituted derivatives thereof, p-aminodiphenyl amine, p-aminodimethyl aniline, p-aminocresol and the like. The term "oxidation hair dye" also embraces a dyeing system containing mixtures of compounds as above described, including systems which include conventional modifiers such as resorcinol, pyrogallol, pyrocatechin, 2-naphthol and the like.

By the use of the term "bleaching solution", it is meant an alkaline aqueous solution of hydrogen peroxide, a compound yielding hydrogen peroxide, a compound yielding hydrogen peroxide in aqueous media, or an ammonium and/or an alkaline metal persulfate, percarbonate, or perborate.

This invention also has application to other hair treatment processes, for example, merely lightening by the action of a bleaching agent, dyeing with a dye, and other processes which utilize, agents which have a tendency to damage hair and make it more porous. Thus the use of the term "bleach compositions", "bleaching solution", "bleaching" is meant to encompass these applications.

The bleaching solutions most commonly used in bleaching or lightening hair is essentially hydrogen peroxide in an alkaline solution with varying amounts of compounds, such as persulfate salts, to accelerate the action of the agent. The strongest of the agents which are currently used for bleaching are sold as powders which are typically mixed with commercially available, e.g., 20 volume, hydrogen peroxide. These are the so called "powder bleaches."

The bleaching solution of this invention is an aqueous based composition, with the terminology being used in its usual generic sense, as inclusive of any water-containing compositions. Thus, this includes true solutions or mixtures of materials dissolved or dispersed in the aqueous medium. The amount of water present in this component can vary over a wide range depending to a large measure on the quantity of the other ingredients.

The bleaching solution used in this invention may have an antioxidant incorporated in it. Useful antioxidants include sodium sulfite, thioglycolic acid, sodium hydrosulfite, and ascorbic acid. Sequestering agents may also be present in the bleaching solution. Useful sequestering agents include ethylene diamine tetraacetic acid, and its various sodium salts, tetrasodium pyrophosphate and the like. Surfactants, additionally, may be present in the bleaching solution and useful surfactants include the anionic, non-ionic and cationic type. Also the bleaching solution may contain dyes, perfumes and conditioners as are conventionally employed in the art.

The quantity of oxidizing agent used will vary according to the particular agent employed and the specific end use of the composition. Generally, the oxidizing agent will be present in the final bleaching solution in the range from about 0.5% to about 20% by weight based upon the total weight of the bleaching solution.

Any of a number of bases, both organic and inorganic, may be used to obtain the suitable pH. By way of example, the following may be mentioned: monoethanolamine, sodium hydroxide, potassium hydroxide, ammonia ($NH_3$), and calcium hydroxide [$Ca(OH)_2$]. Alternately, the alkaline substance can be a lower alkanolamine containing 2 to 4 carbon atoms, for example, monoisopropanolamine, monoethanolamine, monobutanolamine, and the like. Preferred bases are the carbonate powders, for example, sodium carbonate, sodium bicarbonate, and the phosphate powders, for example sodium tripolyphosphate (STP), sodium pyrophosphate.

Various organic solvents may also be present in the bleaching solution for the purpose of solubilizing any of the components which may be insufficiently soluble in the water. Generally, the solvent selected is such as to be miscible with water and innocuous to the skin. Suitable solvents include, for example, ethanol, isopropanol, glycerine, ethylene glycol, propylene glycol, ethylene glycol monoethylether, diethylene glycol, dyethylene glycol monoethylether, etc.

The pH of the bleaching solution will be on the basic side within the range of from about 8 to about 12, with the preferred range of from about 9.5 to about 10.5. Any of a wide variety of alkalizing agents or buffers may be used to maintain the pH within the desired range.

Accordingly, and more specifically, the bleach packet comprises a bleach composition may comprise an oxidation hair dye and an alkaline substance adapted to produce a pH in the range of about 8.0 to about 12.0, and preferably about 10, in the final aqueous bleach solution. Ammonium hydroxide, because of its freedom of toxicity over a wide concentration range, and its economy, is a widely used alkalizing agent. Other compatible ammonia derivatives may be used as the alkalizing agent, for example, alkylamine such as ethylamine; or an alkanolamine, such as monoethanolamine, diethanolamine and aminomethylpropanol. Likewise, any of the common inorganic alkalizing agents may be used, such as sodium or potassium hydroxide, sodium or potassium carbonate, sodium phosphate, sodium hydrogen phosphate, sodium silicate, and the like. Lower alkyl and lower alkanol substituted ammonium hydroxides in which the lower alkyl or lower alkanol portion contains 1 or 2 carbon atoms, for example, tetramethyl ammonium hydroxide, tetraethyl ammonium hydroxide and tetraethanol ammonium hydroxide, and corresponding substituted sulfonium hydroxides, for example, trimethylsulfonium hydroxide, are the full equivalents of ammonia (or ammonium hydroxide) in the invention.

The activator solution used to activate the bleach composition preferably comprises hydrogen peroxide. The amount of hydrogen peroxide will be that reactable with the oxidation hair dye ingredient contained within the package or packages used. When hydrogen peroxide is employed as the activator, the preferred range is from about 2% to about 7% by weight, based upon the total weight of the bleaching solution.

The activator solution comprising, for example, hydrogen peroxide, may also include conventional stabilizers and preservatives for hydrogen peroxide and may, in addition, include an acid ingredient, for example phosphoric acid, in an amount sufficient to impart an acidic pH to the system to effectuate optimum stability of the hydrogen peroxide.

This invention has been described with specific reference to hydrogen peroxide as the agent which oxidizes the hair dye. It is apparent that other substances of like properties can also be used, such as derivatives of hydrogen peroxide, for example, urea hydrogen peroxide and other organic and inorganic peroxides, as well as perbbrates and persulfates, all of which are the full equivalents of hydrogen peroxide in their use.

Various thickening agents may also be incorporated in the aqueous bleaching solution, either included in the packet or in the activator solution. These thickening agents include sodium alganate, gum arabic, cellulose derivatives, such as methyl cellulose, hydroxy ethyl cellulose, etc. Likewise, inorganic thickening agents, such as bentonite, talc and kaolin are useful.

Conditioning additives to make the hair feel better may also be added to bleaching solutions, again, either included in the packet or in the activator solution. Such additives include proteins (animal and vegetable sources), modified proteins, powdered conditioners (difatty quats, quaternized polymers, such as polymer JR, Merquat).

To facilitate the penetration of the active materials into the hair, it may be desirable to also incorporate a swelling agent in the bleaching solution. These materials are generally basic in nature and give the treating solutions a relatively high pH. A pH between 9.5 to 10.5 is particularly suitable for this purpose. However, a pH between approximately 7.0 and 12.0 can be used.

The bleaching solution used herein may also contain many other ingredients conventional in cosmetic products. Again, these ingredients may be contained in the packet or in the activator solution. For example, humectants, fragrances, surfactants and emulsifiers to yield a product with the desired degree of cosmetic elegance for optimum consumer appeal. In the case of oxidation hair dye products, the use of added surfactants of the class conventionally utilized in shampoos permits the creation of hair dyes of the "shampoo-in" type.

The bleach packet comprises an envelope made of a thin film of synthetic organic polymeric material which is soluble in the water into which the bleach additive is to be introduced.

The bleaching composition is packaged, preferably in unit application portions, within at least one sealed, water soluble envelope, pouch or bag. These envelopes are preferably formed of a cold water-soluble polymeric film. The material from which the additive package envelope is formed should be readily soluble in the aqueous activator solution.

Suitable water-soluble polymeric films are those formed from polyvinyl alcohol, preferably plasticized; methyl cellulose; a carboxy methyl cellulose such as sodium carboxy methyl cellulose; sodium carboxy methyl-hydroxy methyl cellulose; a film derivative of polyethylene glycol, or the like. Polyvinyl alcohol (PVA) films are preferred, and particular formulations are disclosed in U.S. Pat. No. 3,413,229 to Bianco, et al; U.S. Pat. No. 3,892,905 to Albert; U.S. Pat. No. 3,374,195 to Bianco, et al; and U.S. Pat. No. 3,300,546 to Baechtold; the disclosures of which are incorporated herein by reference.

Present economics strongly favor polyvinyl alcohol films as the synthetic organic polymeric material for forming the additive package envelope. According to the preferred embodiments of the invention, the polyvinyl alcohol takes the form of a film having a thickness of about 2 mils and preferably between about 1 and 2.0 mils.

Preferably, the PVA is blended with quantities of alternative resins (such as polyvinylpyrrolidone) and plasticisers (generally water soluble such as polyethylene glycols, glycerine, etc.) to aid in the dissolution of the film in water (up to 30%). Water soluble polyvinyl alcohol is generally polyvinyl acetate which has been hydrolyzed to the molar extent of 80-90% and may vary in molecular weight from 15,000 to 150,000. It has been discovered that when the water-soluble polymer is polyvinyl alcohol the hair which is bleached is conditioned by the PVA, i.e. is less frizzy, stringy, etc.

Generally, a film of at least about 2 mm thickness is satisfactory in as so far as solubility is concerned. However, in order to increase the protective or conditioning function of the water soluble polymer enclosure, it may be desirable to either use larger bags so that more polymer is contained in the aqueous solution and/or thicker bags. Thus, for example, increasing the thickness of the bag from 2 mm to, say, 6 mm, and doubling the dimensions of the bag increases the amount of polymer in the same final solution by 12. Thus, a small increase in the size of the bag and the thickness of the material dramatically increases the amount of polymer added to the aqueous bleaching solution. Likewise, an amount of polymer may be added to the packet or activator solution to enhance the conditioning effect.

The bleaching compositions used in the present invention are contained within a single, hermetically sealed, water-soluble envelope. The wall thickness of the envelope may be adjusted over a wide range in order to achieve adequate strength for shipping and storage, achieve rapid dissolution of the envelope when it is introduced into the aqueous activator solution and to provide a sufficient amount of, for example, polyvinyl alcohol film to provide the protection and conditioning required for the hair. To achieve these ends, a wall thickness of 0.25 to 5 mil (millimeters) is employed, preferably 0.5-3 mil, most preferably 1-2 mil. The walls of the envelope are preferably sized so as to dissolve in less than about one minute at ambient water temperatures. Generally, the thinner the film is, the more quickly it would dissolve in the aqueous composition, but the more likely it is to be broken during packaging or storing and handling. Film thickness of about 1 mil have been found to be the most desirable compromise between quick solubility and sufficient mechanical strength. Preferably the bleach packet is formed of a polyvinyl alcohol film having a thickness of about 1.5-3 mils. Preferably this envelope is packaged in such a manner to protect the polyvinyl alcohol envelope from the deleterious effects of environmental moisture or against tearing or puncture during shipping. Overwrap containers may be formed from, for example, polyethylene, metal foil or the like, and packaged with a desiccant to maintain them moisture free.

A water soluble plastic pouch made of PVA, surprisingly, when one considers the reactive nature of the powdered oxidizers, their general degree of reactivity and known instability, has the advantage of showing excellent compatibility with the powdered bleach, i.e. the bleach does not attack the bag and the bag protects the bleach from oxidation. In compatibility tests the active oxygen content of the bleach is unchanged after six months at 37° C. and at least this long at room temperature.

The packets may be filled by methods well known in the art. The additives are placed in the packet and thereafter are sealed by closing and sealing the ends thereof. The packets may be heat sealed or made into the well known "zip-lock" packets.

For example, PVA in tube form is filled with bleaching composition and then sealed using a heat sealer. Care is required during the sealing process to avoid particulate matter from interfering with surfaces to be heat-sealed. The tubes come in differing diameters, with sizes of between 3" and 6" preferred. Excellent stability and performance (e.g. conditioning) has been achieved using films of 2.5 millimeters in thickness. PVA films may also be used in differing thicknesses, e.g., 1.5 to 6.0 mm.

The packages or packets, e.g. from 6 to 36, suitably overwrapped, may then be packaged in a suitable master container (made from glass, plastic, metal, etc.) with a tightly sealed easy-to-reseal lid. A bag of desiccant may be enclosed to help promote the long term stability of the package and to avoid unforeseen problems during usage at the salon. The PVA packages lasts longest when stored under low humidity conditions.

The bleach, when packaged in 30 to 60 gram packets, enables the operator, depending on the effect they are looking for, e.g. streaking, frosting tips, general bleaching, to easily adjust the ratios of bleach to peroxide.

Ideally, the composition in the package should be nonreactive with the envelope material. However, an additive which is reactive with the envelope material may be dispersed, for example, in a nonreactive vehicle such as mineral oil, whereby the reactive particles are coated with the oil and reaction between the envelope and the reactive particles is eliminated or at least substantially alleviated.

This invention also contemplates an additive package which contains a plurality of additives. Where the additives are compatible and nonreactive with each other, they may be admixed directly with each other and placed in an envelope. In some instances, the compatibility of additives obtains only when they are in a dry state. In this event, care should be exercised to place dry additives in the envelope, evacuate air from the envelope, if deemed necessary, and then seal the envelope by heat sealing.

Where the additives to be combined in a single envelope interact with each other, it is contemplated that they may be physically separated, yet within the same envelope. This can be accomplished by utilizing one envelope within another, or by coating one or both of the materials with an inert, temporary protective covering. It will be appreciated that a plurality of separate envelopes may also be employed to hold different additives which would be troublesome to hold any single envelope.

The concentration of the oxidizing agent in the bleaching solutions applied to the hair will vary with the particular type of application involved, e.g. bleaching, tinting, coloring, e.g. the specific oxidizing agent, as well as other factors. Where the oxidizing agents serves as a bleach, its concentrations will be very high and may approach saturated solutions. In the case where the oxidizing agent serves as the agent by developing the color for an oxidation dye, the values will be much lower. In this case it may vary from about 0.5% to about 15% by weight.

The quantity of water soluble polymer, for example polyvinyl alcohol, contained in the bleaching solution will vary depending on the particular use for which the composition is designed, and depending upon the particular bleaching composition employed, and the conditioning desired. Generally, it has been found that from about 0.25% to 7% by weight, based upon the total weight of the bleaching solution is effective, from about 0.5% to about 1.5% preferred.

The preferred method of using these products is as for one application of average length hair (obviously more is required for extra long hair and less will be required for a streaking effect) is a packet of powdered bleach (roughly 1 oz.) is stirred into 2-3 ounces of activator solution, typically hydrogen peroxide, normally stabilized, which is 20, 40 or 50 volume in activity. The packet is contacted with preferably immersed below the surface of the activator solution. The time during which the bleaching composition is allowed to mix with the activator will vary. In general, however, this will be between 5 to 60 minutes.

It is to be understood that the invention is not to be limited to the exact compositions shown and described, as obvious modifications and equivalents will be apparent to one skilled in the art, and the invention is therefore to be limited only by the scope of the appended claims.

The following examples are further illustrative of the present invention. It should be understood, however, that the invention is not limited thereto.

EXAMPLES

Example 1-4

Powdered bleach compositions were made and placed in PVA packets. The bleach compositions contained oxidizing agents, e.g. persulfates and perborates, gums for making the final product viscous and easy to apply, a foaming agent to enhance spreadability, and bulking agents (fillers) such as silicates. Fumed silica was used to keep the formulations dry and dust free.

| Typical Examples: | 1 | 2 | 3 | 4 |
|---|---|---|---|---|
| Potassium Persulfate | 30.0% | 25.0% | 10.0% | 0.0% |
| Ammonium Persulfate | 20.0 | 25.0 | 30.0 | 35.0 |
| Sodium Persulfate | 5.0 | 0.0 | 10.0 | 3.0 |
| Sodium Perborate | 0.0 | 5.0 | 5.0 | 10.0 |
| Sodium Silicate | 10.0 | 5.0 | 10.0 | 10.0 |
| Sodium Metasilicate | 10.0 | 20.0 | 10.0 | 10.0 |
| Sodium Lauryl Sulfate (powder) | 1.0 | 1.0 | 1.0 | 1.0 |
| Sodium Stearate | 8.0 | 8.0 | 8.0 | 10.0 |
| Sodium Carboxymethylcellulose | 10.0 | 5.0 | 10.0 | 5.0 |
| Tetrasodium EDTA | 1.0 | 1.0 | 1.0 | 1.0 |
| Silica (Cabosil) | 5.0 | 5.0 | 5.0 | 5.0 |

These bleach compositions were made in either the snow white form (no color additives), or made blue to heighten the brightness of the hair after bleaching.

Example 5

An additional series of tests were performed using commercially available powdered bleaches. Thirty (30) grams of each bleach were packaged in a water-soluble PVA packet, (5 cm × 10 cm, and 2.5 mils thick). The packet when dissolved in the activator solution (6% $H_2O_2$) did not produce any dust fumes. There was a dramatic improvement in the condition of the hair after the bleaching, as far as its feel and condition were concerned.

This clearly demonstrates that any commercially available hair bleach can be dramatically improved in performance by this novel means of packaging, both from a use viewpoint (no dust fumes) and from a conditioning viewpoint (the final results and general appearance of the consumer's hair).

Example 6

A test was run where the 2 grams of PVA (tradename-Evanol, from Allied Chemical) was mixed into 30 grams of the powdered bleach of Example 3 and then used in the conventional manner, i.e., 30 g were dissolved in a 6% peroxide activator solution. Intense dust fumes were noted. The evaluators, in blind tests, were able to easily pick out the improved conditioning benefits, particularly the after-feel to the hair, produced by the PVA coating from the water-soluble PVA.

Example 7

Another test was performed using the same test condition of Example 6, except a 70/30 combination of PVA (Evanol) and PVP (PVP K-90 ex GAF). Intense dust fumes were noted and the same conditioning benefits were obtained as noted in Example 6.

Example 8 a. Numerous stability trials were carried out where PVA packets containing 60 and 30 grams of powdered bleach, similar to Example 3 were subjected to storage conditions of 45° C. and 37° C. for a period of six months. No signs of package incompatibility and no discernible loss in product efficacy were noted when the packets were dissolved in a 6% activator solution of $H_2O_2$. Surprisingly, the high temperature stability test samples performed better, in that they dissolved faster in the activator solution.

b. Freeze thaw tests were run on similar packets. The packets were put in a freezer (−20° C.) and after 24 hours were exposed to 37° C. environment. This freeze-thaw cycling process was repeated several times. The bags maintained their integrity and there was no loss in product efficacy when dissolved in the activator solution.

c. Product efficacy was checked at the end of each of the aforedescribed stability trials. The bags were dissolved in the activator solution and a series of user trials were carried out. These tests showed that the performance of the aged bags containing bleach was equivalent to those of the bags which were freshly filled. The users and operators commented on the superior feel and appearance of the hair due to the conditioning effect of the PVA used as the material of the bag.

What is claimed:

1. A method of bleaching and conditioning hair comprising:
    (a) providing a bleaching packet comprising a predetermined effective amount of hair bleach composition to bleach a person's hair, enclosed in a water soluble polymer enclosure comprising a polyvinyl alcohol, (PVA), the PVA effective, when dissolved, for conditioning a person's hair;
    (b) providing an activator solution comprising water and an effective amount of a hydrogen peroxide or a hydrogen peroxide releasing composition activator to activate the bleach and dissolve the water soluble polymer enclosure;
    (c) contacting bleach packet with the activator solution to thereby dissolve the water soluble polymer enclosure and activate the bleach to form a bleach solution containing PVA for conditioning a person's hair;

(d) applying the bleach solution to a person's hair whereby the activated bleach bleaches the hair and the PVA conditions the hair.

2. The method of claim 1, wherein the activator is hydrogen peroxide.

3. The method of claim 1, wherein the step of contacting comprises immersing the bleach packet in the activator solution.

4. The method of claim 1, wherein the bleach composition comprises an oxidation hair dye.

5. The method of claim 1, wherein the packet is enclosed in an air and water impervious enclosure.

* * * * *